(12) United States Patent
Hart et al.

(10) Patent No.: US 11,819,208 B2
(45) Date of Patent: Nov. 21, 2023

(54) HANDHELD ELECTROMECHANICAL SURGICAL DEVICE WITH STRAIN GAUGE DRIFT DETECTION

(71) Applicant: Covidien LP, Mansfield, MA (US)

(72) Inventors: Alexander J. Hart, Tolland, CT (US); James P. Delbo, North Haven, CT (US); Charles R. Kollar, Washington, DC (US); Haley E. Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 36 days.

(21) Appl. No.: 17/395,309

(22) Filed: Aug. 5, 2021

(65) Prior Publication Data
US 2023/0038322 A1   Feb. 9, 2023

(51) Int. Cl.
*A61B 17/068* (2006.01)
*A61B 17/34* (2006.01)
*A61B 17/00* (2006.01)

(52) U.S. Cl.
CPC ........ *A61B 17/068* (2013.01); *A61B 17/3476* (2013.01); *A61B 2017/00115* (2013.01); *A61B 2017/00398* (2013.01); *A61B 2560/0223* (2013.01); *A61B 2560/0276* (2013.01); *A61B 2562/0261* (2013.01)

(58) Field of Classification Search
CPC ............... A61B 17/068; A61B 17/072; A61B 2017/00115; A61B 2560/0276; A61B 2017/00017
See application file for complete search history.

(56) References Cited

U.S. PATENT DOCUMENTS

| 3,193,165 | A | 7/1965 | Akhalaya et al. |
| 3,388,847 | A | 6/1968 | Kasulin et al. |
| 3,552,626 | A | 1/1971 | Astafiev et al. |
| 3,622,275 | A | 11/1971 | Staunton et al. |
| 3,638,652 | A | 2/1972 | Kelley |

(Continued)

FOREIGN PATENT DOCUMENTS

| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Gloria R Weeks
(74) *Attorney, Agent, or Firm* — Carter, DeLuca & Farrell LLP

(57) ABSTRACT

According to one embodiment of the present disclosure, a surgical device is disclosed. The surgical device includes a motor and a transmission assembly movable by the motor. The surgical device also includes a force sensor configured to measure force imparted on the transmission assembly. The device may also include a controller configured to: control the motor to move the transmission assembly to a starting position, interrogate the force sensor to receive a sensor signal, compare the sensor signal to a threshold, and determine whether the force sensor is faulty based on the comparison of the sensor signal to the threshold.

20 Claims, 8 Drawing Sheets

(56) References Cited

U.S. PATENT DOCUMENTS

| | | | |
|---|---|---|---|
| 3,771,526 A | 11/1973 | Rudie | |
| 4,198,982 A | 4/1980 | Ortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,017,354 A | 1/2000 | Culp et al. | |
| 6,024,748 A | 2/2000 | Manzo et al. | |
| 6,025,683 A | 2/2000 | Philipp | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,090,123 A | 7/2000 | Culp et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,237,604 B1 | 5/2001 | Burnside et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |

(56) References Cited

U.S. PATENT DOCUMENTS

| | | |
|---|---|---|
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,565 B1 | 2/2003 | Whitman et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,556,778 B2 | 4/2003 | Zhang et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,611,793 B1 | 8/2003 | Burnside et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,940,255 B2 | 9/2005 | Loch |
| 6,942,675 B1 | 9/2005 | Vargas |
| 6,945,444 B2 | 9/2005 | Gresham et al. |
| 6,953,138 B2 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,126,310 B1 | 10/2006 | Barron |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,193,519 B2 | 3/2007 | Root et al. |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,117 B2 | 10/2007 | Krueger et al. |
| 7,285,125 B2 | 10/2007 | Viola |
| 7,285,177 B2 | 10/2007 | Bushoff et al. |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,362,062 B2 | 4/2008 | Schneider et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,400,107 B2 | 7/2008 | Schneider et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,514,890 B2 | 4/2009 | Schneider et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,638,958 B2 | 12/2009 | Philipp et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,738,971 B2 | 6/2010 | Swayze et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,784,663 B2 | 8/2010 | Shelton, IV |

(56) References Cited

U.S. PATENT DOCUMENTS

| | | |
|---|---|---|
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 7,998,157 B2 | 8/2011 | Culp et al. |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,154,239 B2 | 4/2012 | Katsuki et al. |
| 8,157,153 B2 | 4/2012 | Shelton, IV et al. |
| 8,161,977 B2 | 4/2012 | Shelton, IV et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,210,411 B2 | 7/2012 | Yates et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,375,808 B2 | 2/2013 | Blumenkranz et al. |
| 8,399,822 B2 | 3/2013 | Al-Ali |
| 8,400,108 B2 | 3/2013 | Powell et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,473,502 B2 | 6/2013 | Ledford et al. |
| 8,485,414 B2 | 7/2013 | Criscuolo et al. |
| 8,490,853 B2 | 7/2013 | Criscuolo et al. |
| 8,500,769 B2 | 8/2013 | Deng |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,627,995 B2 | 1/2014 | Smith et al. |
| 8,631,993 B2 | 1/2014 | Kostrzewski |
| 8,636,187 B2 | 1/2014 | Tueil et al. |
| 8,640,940 B2 | 2/2014 | Ohdaira |
| 8,657,174 B2 | 2/2014 | Yates et al. |
| 8,662,370 B2 | 3/2014 | Takei |
| 8,663,258 B2 | 3/2014 | Bettuchi et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,708,213 B2 | 4/2014 | Shelton, IV et al. |
| 8,733,611 B2 | 5/2014 | Milliman |
| 8,746,532 B2 | 6/2014 | Nalagatla et al. |
| 8,806,973 B2 | 8/2014 | Ross et al. |
| 8,808,311 B2 | 8/2014 | Heinrich et al. |
| 8,893,946 B2 | 11/2014 | Boudreaux et al. |
| 8,959,617 B2 | 2/2015 | Newlin et al. |
| 8,989,903 B2 | 3/2015 | Weir et al. |
| 9,017,851 B2 | 4/2015 | Felder et al. |
| 9,084,601 B2 | 7/2015 | Moore et al. |
| 9,089,338 B2 | 7/2015 | Smith et al. |
| 9,095,339 B2 | 8/2015 | Moore et al. |
| 9,113,874 B2 | 8/2015 | Shelton, IV et al. |
| 9,142,992 B2 | 9/2015 | Malackowski et al. |
| 9,226,750 B2 | 1/2016 | Weir et al. |
| 9,326,769 B2 | 5/2016 | Shelton, IV et al. |
| 9,326,770 B2 | 5/2016 | Shelton, IV et al. |
| 9,364,249 B2 | 6/2016 | Kimball et al. |
| 9,393,017 B2 | 7/2016 | Flanagan et al. |
| 9,398,911 B2 | 7/2016 | Auld |
| 9,439,651 B2 | 9/2016 | Smith et al. |
| 9,498,219 B2 | 11/2016 | Moore et al. |

(56) References Cited

U.S. PATENT DOCUMENTS

| | | | |
|---|---|---|---|
| 10,271,851 B2 | 4/2019 | Shelton, IV et al. |
| 10,292,704 B2 | 5/2019 | Harris et al. |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0102472 A1 | 5/2007 | Shelton |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0270355 A1* | 10/2010 | Whitman ............ A61B 17/072 |
| | | | 227/176.1 |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0257636 A1 | 10/2011 | Whitman et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0200621 A1* | 7/2014 | Malackowski ........ A61B 34/20 |
| | | | 606/86 R |
| 2015/0374371 A1 | 12/2015 | Richard et al. |
| 2016/0066916 A1* | 3/2016 | Overmyer ............ H02H 3/207 |
| | | | 227/176.1 |
| 2016/0095585 A1 | 4/2016 | Zergiebel et al. |
| 2016/0106406 A1 | 4/2016 | Cabrera |
| 2016/0143641 A1 | 5/2016 | Sapienza et al. |
| 2016/0157856 A1 | 6/2016 | Williams et al. |
| 2016/0174977 A1* | 6/2016 | Lytle, IV ............. A61B 90/03 |
| | | | 227/180.1 |
| 2016/0174988 A1 | 6/2016 | D'Agostino et al. |
| 2016/0249945 A1 | 9/2016 | Shelton, IV et al. |
| 2016/0302792 A1 | 10/2016 | Motai |
| 2016/0310134 A1* | 10/2016 | Contini ............ A61B 17/07207 |
| 2018/0168625 A1* | 6/2018 | Posada ................. A61B 34/30 |
| 2020/0367891 A1* | 11/2020 | Kollar ............... A61B 17/1155 |
| 2022/0202488 A1* | 6/2022 | Shelton, IV ....... H01R 13/6581 |

FOREIGN PATENT DOCUMENTS

| | | |
|---|---|---|
| CN | 103 622 727 A | 3/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138818 A2 | 12/2009 |
| EP | 2168510 A1 | 3/2010 |
| EP | 2238926 A2 | 10/2010 |
| EP | 2524656 A2 | 11/2012 |
| EP | 2684529 A2 | 1/2014 |
| EP | 2954854 A2 | 12/2015 |
| EP | 3011915 A2 | 4/2016 |
| EP | 3078335 A1 | 10/2016 |
| EP | 3103402 A1 | 12/2016 |
| EP | 3165180 A2 | 5/2017 |
| EP | 3175800 A1 | 6/2017 |
| EP | 3231374 A1 | 10/2017 |
| EP | 3593736 A2 | 1/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

(56) References Cited

FOREIGN PATENT DOCUMENTS

WO          201617194 A1    10/2016
WO       2020014056 A1    1/2020

OTHER PUBLICATIONS

European Examination Report from Appl. No. 14181908.6 dated May 3, 2016.
Extended European Search Report dated Nov. 6, 2018 issued in corresponding EP Appln. No. EP18176772.4.
European Examination Report dated Oct. 4, 2019 issued in corresponding EP Appln. No. 18176772.4.
Partial European Search Report dated May 8, 2020 issued in corresponding EP Appln. No. 20154026.7.
Extended European Search Report dated May 8, 2020 issued in corresponding EP Appln. No. 20154027.5.
European Examination Report dated Apr. 22, 2020 issued in corresponding EP Appln. No. 18176772.4.
Extended European Search Report dated Jul. 29, 2020 issued in corresponding EP Appln. No. 20154026.7.
Extended European Search Report dated Oct. 31, 2018 issued in corresponding EP Appln. No. 18176776.5.
European Examination Report dated Oct. 23, 2019 issued as EP Application No. 18176776.5.
European Examination Report issued in corresponding application EP 18176776.5 dated Jan. 27, 2021 10 pages).
Uropean Examination Report dated Apr. 22, 2020 issued in corresponding EP Appln. No. 18176772.4.
Extended European Search Report dated Nov. 6, 2018 issued in corresponding EP Appln. No. EP18176772.4.
International Search Report and Written Opinion of the International Searching Authority issued in corresponding application PCT/IB2022/057159 dated Oct. 31, 2022 (12 pages).

\* cited by examiner

HANDHELD ELECTROMECHANICAL SURGICAL DEVICE WITH STRAIN GAUGE DRIFT DETECTION

BACKGROUND

Circular staplers are used in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument through an incision and toward the transected rectum portion. The physician may then introduce the remainder of the circular stapling instrument (including the cartridge assembly) into a rectum of a patient and maneuver the device up the colonic tract of the patient toward the transected rectum portions. The anvil and cartridge assemblies are approximated toward one another, and staples are ejected from the cartridge assembly toward the anvil assembly to form the staples in tissue to affect an end-to-end anastomosis, and an annular knife is advanced to core a portion of the clamped tissue portions. After the end-to-end anastomosis has been affected, the circular stapling apparatus is removed from the surgical site.

Powered electromechanical surgical staplers, including battery power sources, utilize motors to actuate various components of the powered surgical stapler during clamping, stapling, and cutting portions of the anastomosis procedure. Such staplers utilize various sensors, including strain gauges, which might fail overtime and output erroneous readings. Thus, there is a need for a system and method to detect and deal with sensor drift.

SUMMARY

The present disclosure provides a powered surgical stapler configured to clamp, staple, and cut tissue. The powered surgical stapler includes a force sensor, such as a strain gauge, that is used to provide force feedback. Thus, sensor data allows for safe operation of each of the phases, namely, clamping, stapling, and cutting. Since the sensor, such as a strain gauge, is an analog sensor the signal output is very weak and as such is easily affected by environmental factors, such as water ingress, detergent deposits, and humidity within the operating room. Thus, an early warning detection of irregular sensor signals is useful to preoperatively minimize patient risk.

The powered surgical stapler includes a controller configured to execute a monitoring algorithm, which may be embodied as software instructions. The algorithm monitors sensor data for any unexpectedly high values, which might be due to strain gauge drift across autoclave cycles. If such a value is detected, the controller flags this as an error and prevents firing of staples from occurring with the potentially defective strain gauge. The monitoring for the error may occur when no force is expected to be measured, such as while a trocar is fully retracted. The monitoring algorithm is expecting no sensor signal due to a no-load condition and evaluate the incoming sensor signal if an absolute value threshold of a set value is met after a successful calibration. In the that a drift is greater than the specified threshold, the user may be notified via an audio and/or visual alarm and further operation of the powered surgical stapler is prevented.

According to one embodiment of the present disclosure, a surgical device is disclosed. The surgical device includes a motor and a transmission assembly movable by the motor. The surgical device also includes a force sensor configured to measure force imparted on the transmission assembly. The device may also include a controller configured to: control the motor to move the transmission assembly to a starting position, interrogate the force sensor to receive a sensor signal, compare the sensor signal to a threshold, and determine whether the force sensor is faulty based on the comparison of the sensor signal to the threshold.

Implementations of the above embodiment may include one or more of the following features. According to one aspect of the above embodiment, the force sensor may be a strain gauge. The controller may be further configured to determine whether the strain gauge has strain gauge drift. The starting position may be a position at which the transmission assembly is under no mechanical load. The controller may be further configured to obtain an absolute value of the sensor signal and compare the absolute value to the threshold. The surgical device may include a display. The controller may be further configured to output an indication that the force sensor is faulty on the display. The controller may be further configured to prevent operation of the motor in response to the force sensor being faulty. The surgical device may also include a trocar assembly coupled to the transmission assembly and a reload may include a plurality of staples.

According to another embodiment of the present disclosure, a surgical device is disclosed. The surgical device includes an adapter assembly having a transmission assembly and a force sensor configured to measure force imparted on the transmission assembly. The surgical device may also include a handle assembly having a motor configured to move the transmission assembly and a controller, which may be configured to: control the motor to move the transmission assembly to a starting position, interrogate the force sensor to receive a sensor signal, compare the sensor signal to a threshold, and determine whether the force sensor is faulty based on the comparison of the sensor signal to the threshold.

Implementations of the above embodiment may include one or more of the following features. According to one aspect of the above embodiment, the force sensor may be a strain gauge. The controller may be further configured to determine whether the strain gauge has strain gauge drift. The starting position may be a position at which the transmission assembly is under no mechanical load. The controller may be further configured to obtain an absolute value of the sensor signal and compare the absolute value to the threshold. The surgical device may include a display. The controller may be further configured to output an indication that the force sensor is faulty on the display. The controller may be further configured to prevent operation of the motor in response to the force sensor being faulty. The surgical device may also include a trocar assembly coupled to the transmission assembly and a reload may include a plurality of staples. The adapter assembly may also include a storage device and the controller may be configured to store a fault code pertaining to force sensor being fault on the storage device.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
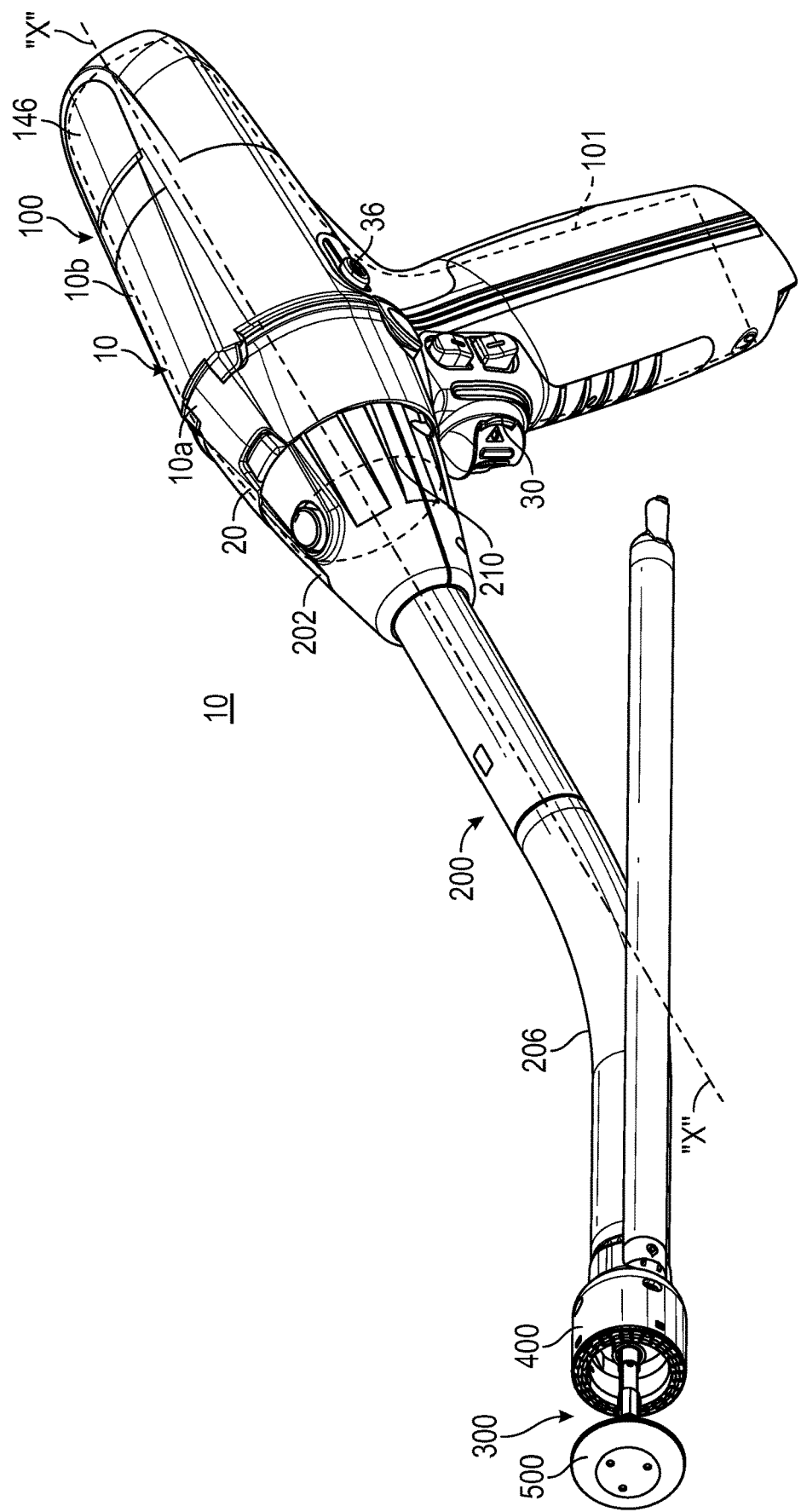
FIG. 1 is a perspective view of a handheld surgical instrument including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered surgical stapler 10 having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical device, such as, for example, a powered surgical stapler 10 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing 11 configured to selectively receive and encase power handle 101. The shell housing 11 includes a distal half-section 10a and a proximal half-section 10b pivotably connected to distal half-section 10a. When joined, distal and proximal half-sections 10a, 10b define a shell cavity therein in which power handle 101 is disposed.

Distal and proximal half-sections 10a, 10b of shell housing 11 are divided along a plane that traverses a longitudinal axis "X" of adapter assembly 200. Distal half-section 10a of shell housing 11 defines a connecting portion 20 configured to accept a corresponding drive coupling assembly 210 (FIG. 3) of adapter assembly 200. Distal half-section 10a of shell housing 11 supports a toggle control button 30. Toggle control button 30 is capable of being actuated in four directions (e.g., a left, right, up and down).

Figure 2:
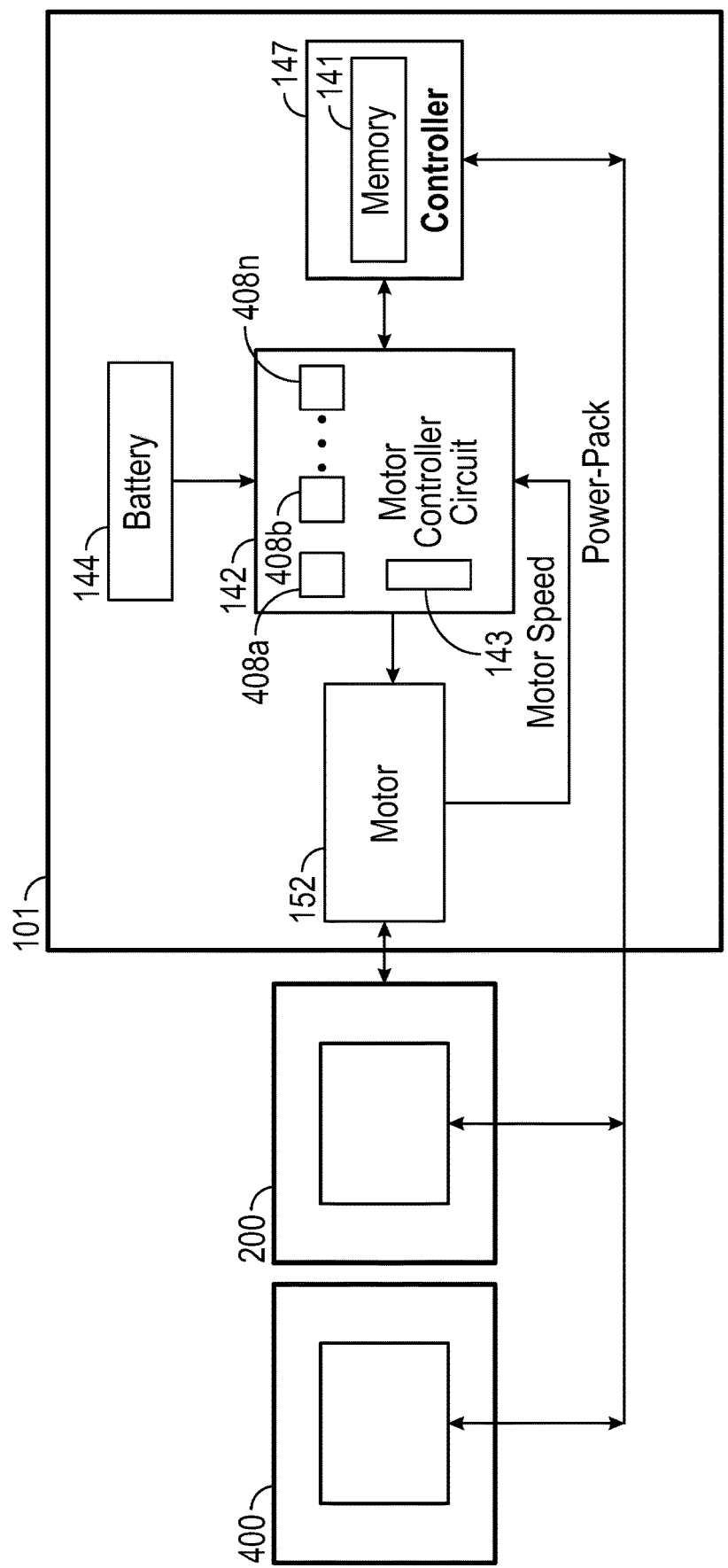
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a plurality of motors 152 coupled to the battery 144. The power handle 101 also includes a display 146. In embodiments, the motors 152 may be coupled to any suitable power source configured to provide electrical energy to the motor 152, such as an AC/DC transformer. Each of the motors 152 is coupled a motor controller 143 which controls the operation of the corresponding motor 152 including the flow of electrical energy from the battery 144 to the motor 152. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408a . . . 408n configured to measure operational states of the motor 152 and the battery 144. The sensors 408a-n include a strain gauge 408b and may also include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. The sensor 408a also includes an encoder configured to count revolutions or other indicators of the motor 152, which is then use by the main controller 147 to calculate linear movement of components movable by the motor 152. Angular velocity may be determined by measuring the rotation of the motor 152 or a drive shaft (not shown) coupled thereto and rotatable by the motor 152. The position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motor 152.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408b of the adapter assembly 200 using a wired or a wireless connection and is configured to receive strain measurements from the strain gauge 408b which are used during operation of the power handle 101.

The power handle 101 includes a plurality of motors 152 each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100. In particular, motors 152 of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fire an annular array of staples 423 of reload 400, and move an annular knife (not explicitly shown) of reload 400.

The reload 400 includes a storage device 402 configured to store operating parameters of the reload 400 including starting clamping force, maximum clamping force, a force factor, and the like. Each type of reload 400 may have a corresponding starting clamping force, which the main controller 147 may obtain automatically by reading the starting clamping force value from the storage device 402 and/or set manually by the user by selecting either the type of the reload 400 or the clamping force directly. Starting clamping force may be any suitable threshold from about 100 pounds to about 200 pounds, in embodiments, the target clamping force may be approximately 150 pounds. In embodiments, a 33 mm sized reload 400 may have a clamping force of about 150 lbs.

Figure 3:
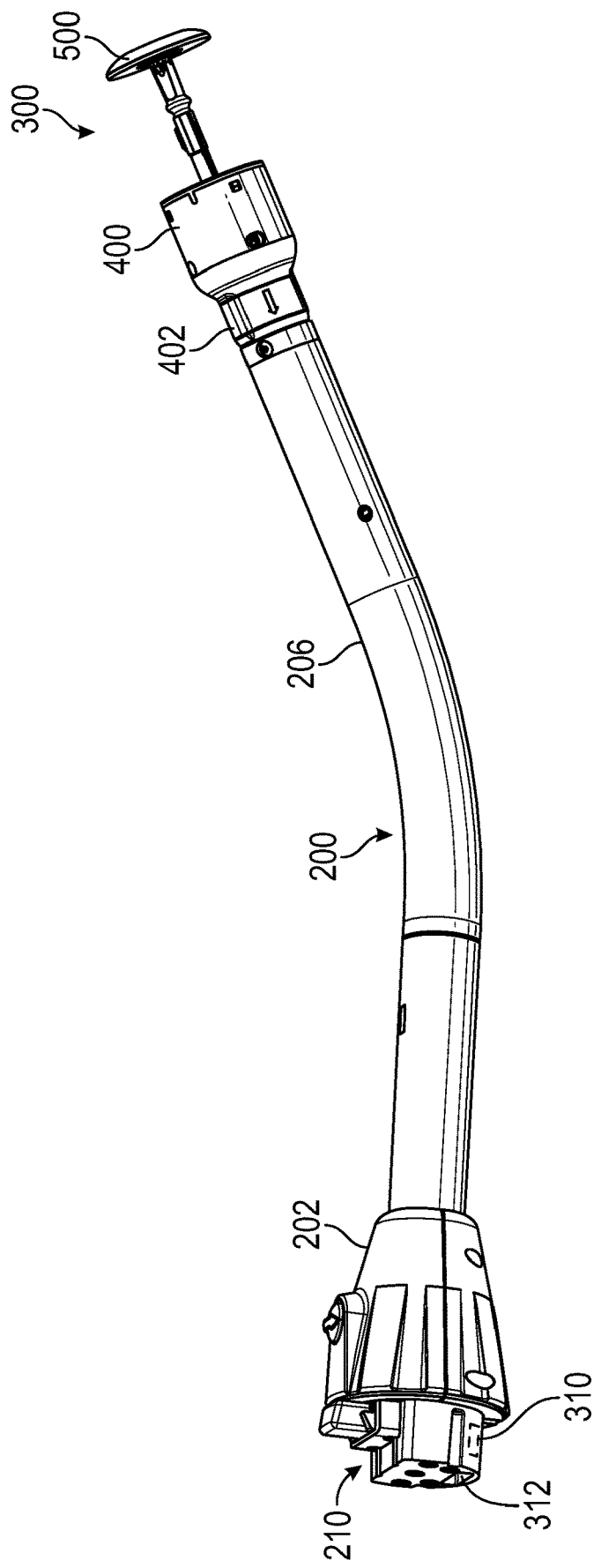
FIG. 3 is a side perspective view of the adapter assembly and the end effector, an annular reload and an anvil assembly, attached to the adapter assembly of FIG. 1 according to an embodiment of the present disclosure.
Figure 4:
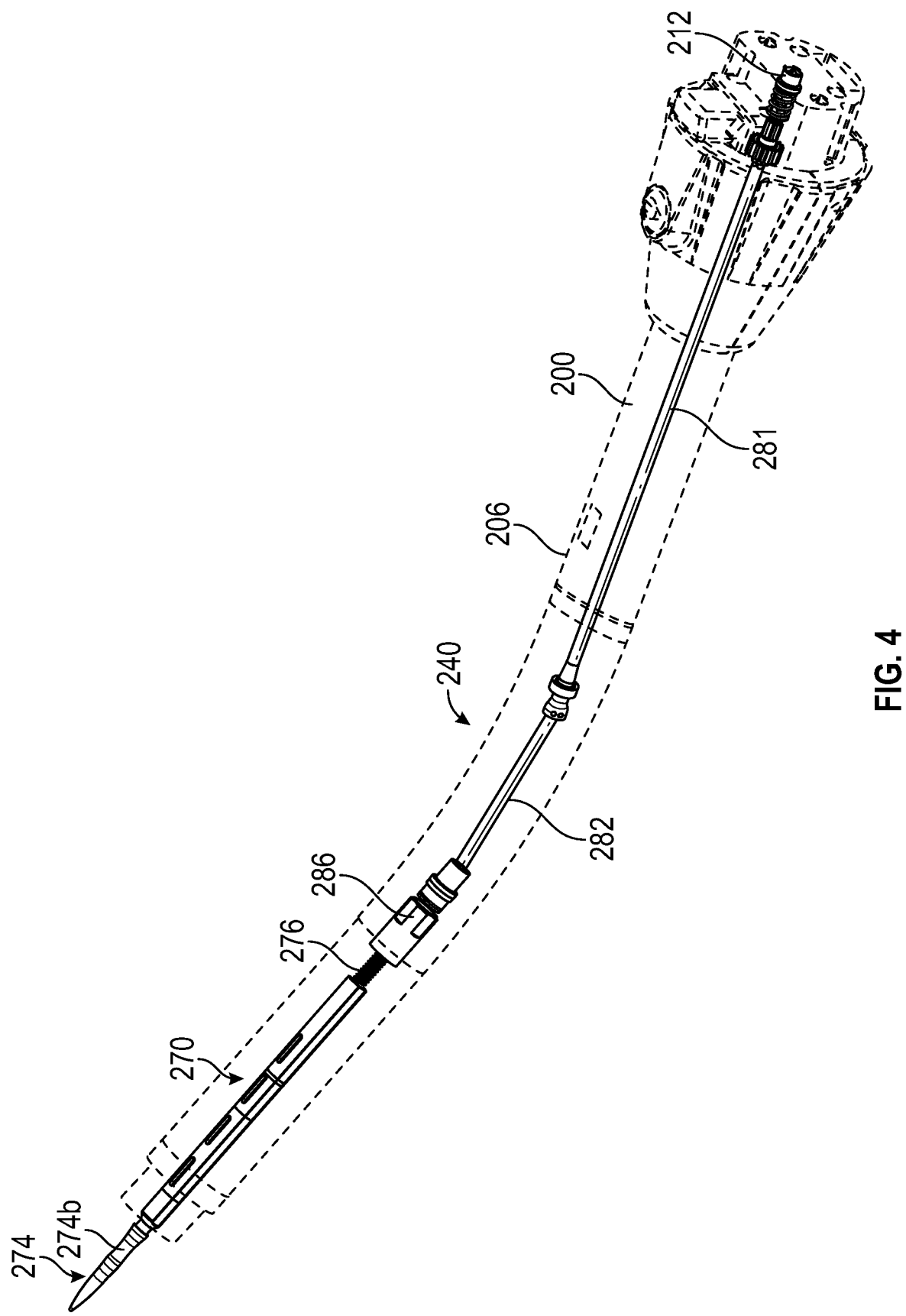
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly (not explicitly shown) of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to one of the motors 152, a second rotatable proximal drive shaft 281, a rotatable distal drive shaft 282, and a coupling member 286, each of which are supported within the outer tube 206 of adapter assembly 200. Clamping transmission assembly 240 functions to extend/retract trocar member 274 of trocar assembly 270 of adapter assembly 200, and to open/close the anvil assembly 510 when anvil assembly 510 is connected to trocar member 274.

Figure 5:
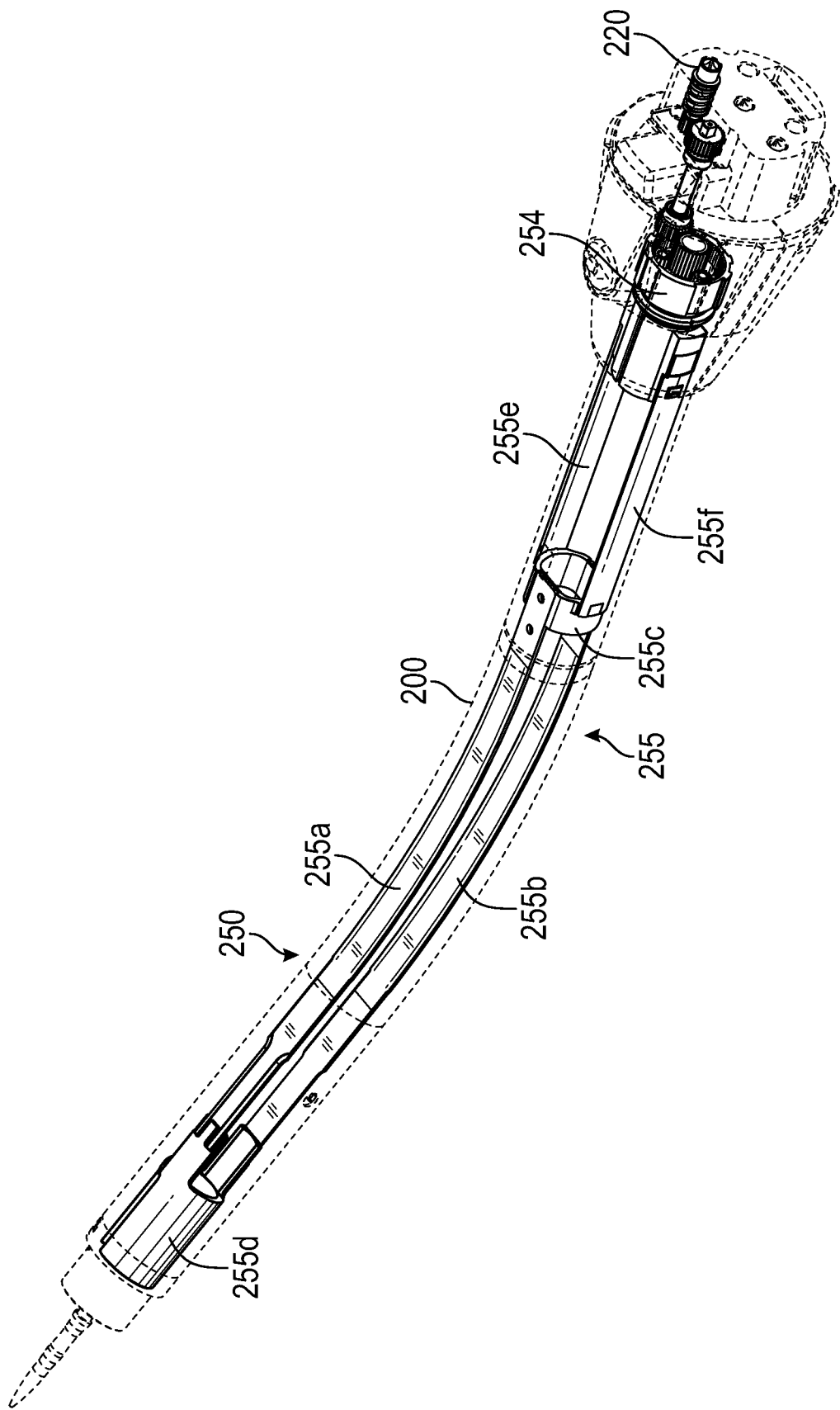
FIG. 5 is a perspective view of a stapling transmission assembly disposed within the adapter assembly of FIG. 1, shown partially in phantom.

With reference to FIG. 5, the adapter assembly 200 includes a stapling transmission assembly 250 for interconnecting one of the motors 152 and a second axially translatable drive member of reload 400, wherein the stapling transmission assembly 250 converts and transmits a rotation of one of the motors 152 to an axial translation of an outer flexible band assembly 255 of adapter assembly 200, and in turn, the staple driver 430 of reload 400 to fire staples 423 from the reload 400 and against anvil assembly 510.

The stapling transmission assembly 250 of adapter assembly 200 includes the outer flexible band assembly 255 secured to staple driver coupler 254. A second rotatable proximal drive shaft 220 is coupled to one of the motors 152 and is configured to actuate that staple driver coupler 254, which converts rotational movement into longitudinal movement. Outer flexible band assembly 255 includes first and second flexible bands 255a, 255b laterally spaced and connected at proximal ends thereof to a support ring 255c and at distal ends thereof to a proximal end of a distal pusher 255d. Each of first and second flexible bands 255a, 255b is attached to support ring 255c and distal pusher 255d. Outer flexible band assembly 255 further includes first and second connection extensions 255e, 255f extending proximally from support ring 255c. First and second connection extensions 255e, 255f are configured to operably connect outer flexible band assembly 255 to staple driver coupler 254 of stapling transmission assembly 250.

Figure 6:
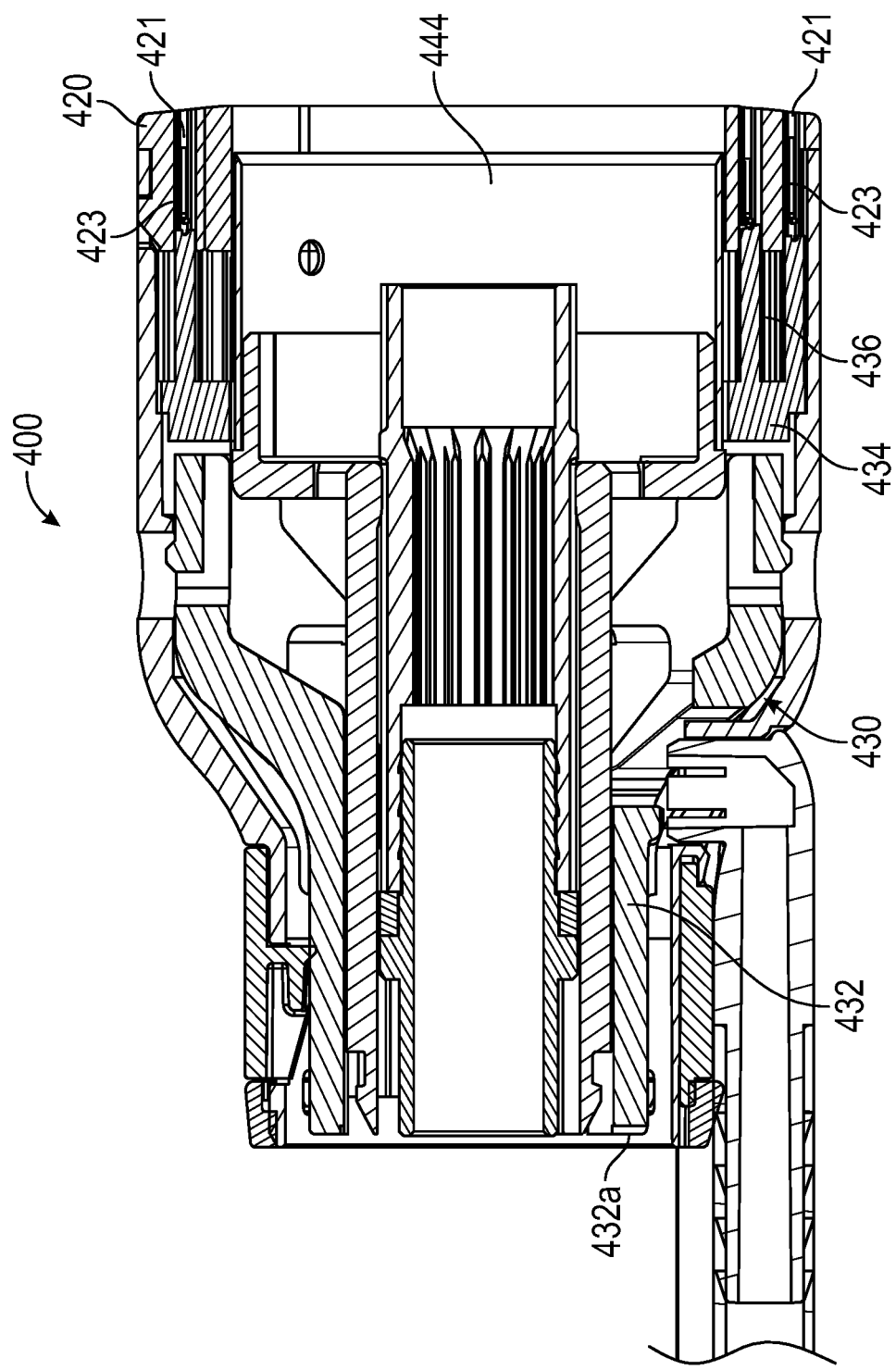
FIG. 6 is a cross-sectional view of a reload of the end effector of FIG. 1.

With reference to FIG. 6, staple driver 430 of reload 400 includes a staple cartridge 420 having a driver adapter 432 and a driver 434. A proximal end 432a of driver adapter 432 is configured for selective contact and abutment with distal pusher 255d of outer flexible band assembly 255 of stapling transmission assembly 250 of adapter assembly 200. In operation, during distal advancement of outer flexible band assembly 255, as described above, distal pusher 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

Forces during an actuation of trocar member 274, closing of end effector 300 (e.g., a retraction of anvil assembly 500 relative to reload 400), and ejecting staples 423 from the reload 400, and advancement of the knife assembly 440 may be measured by the strain gauge 408b in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 7:
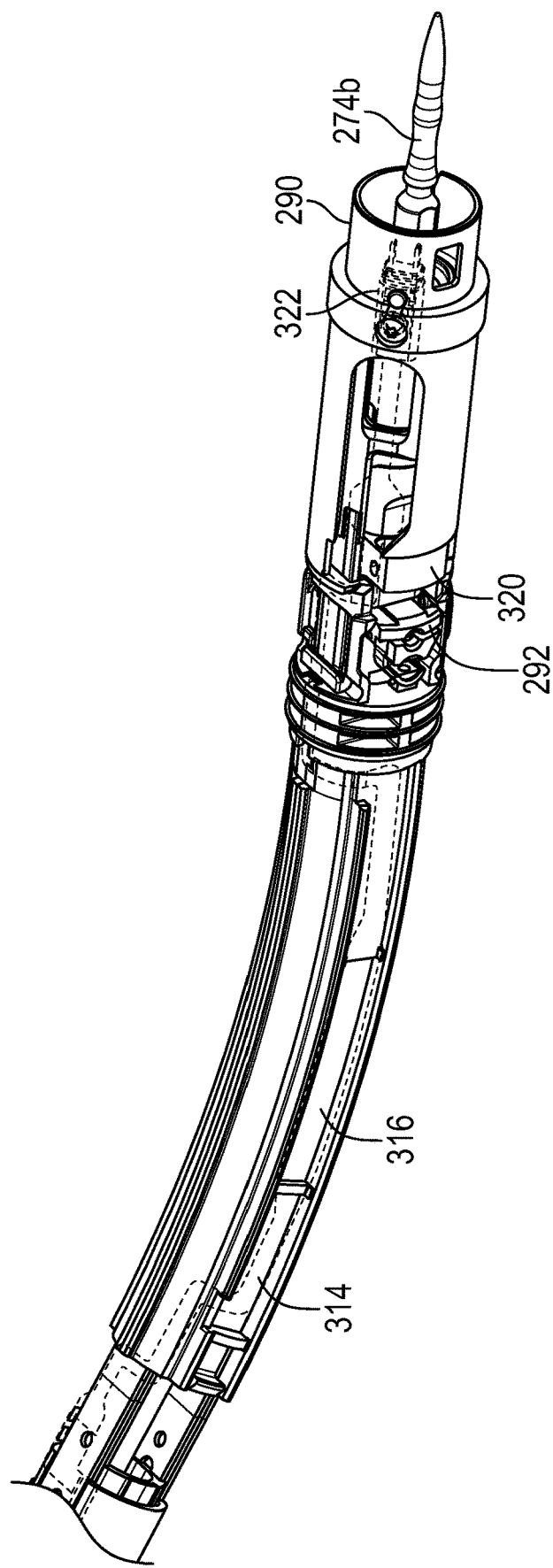
FIG. 7 is a perspective view of the adapter assembly, shown partially disassembled, with a strain gauge assembly.

With reference to FIG. 7, the strain gauge 408b of adapter assembly 200 is disposed within a strain gauge housing 320. The strain gauge 408b measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408*b*. The strain gauge 408*b* then communicates signals to main controller circuit board 142 of power handle 101 of handle assembly 100. Graphics are then displayed on the display 146 of handle assembly 100 to provide the user with real-time status information as shown in FIG. 10.

The trocar assembly 270 is axially and rotationally fixed within outer tube 206 of adapter assembly 200. With reference to FIG. 6, adapter assembly 200 includes a support block 292 fixedly disposed within outer tube 206. The strain gauge housing 320 is disposed between the support block 292 and a connector sleeve 290. The reload 400 is removably coupled to the connector sleeve 290.

In operation, strain gauge 408*b* of adapter assembly 200 measures and monitors the retraction of trocar member 274, which passes through the strain gauge 408*b*. The strain gauge 408*b* of adapter assembly 200 also measures and monitors ejection of the staples 423 from the reload 400, since the first and second flexible bands 255*a*, 255*b* also pass through the strain gauge 408*b*. During clamping, stapling and cutting, a reaction force is exerted on anvil assembly 500 and the reload 400, which is communicated to support block 292, which then communicates the reaction force to a strain sensor of the strain gauge 408*b*.

Strain sensor of strain gauge 408*b* may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408*b* provides a closed-loop feedback to a firing/clamping load exhibited by first, second and third force/rotation transmitting/converting assemblies.

Strain sensor of strain gauge 408*b* then communicates signals to main controller circuit board 142. Graphics are then displayed on display 146 of handle assembly 100 to provide the user with real-time information related to the status of the firing of handle assembly 100. Strain gauge 408*b* is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

Figure 8:
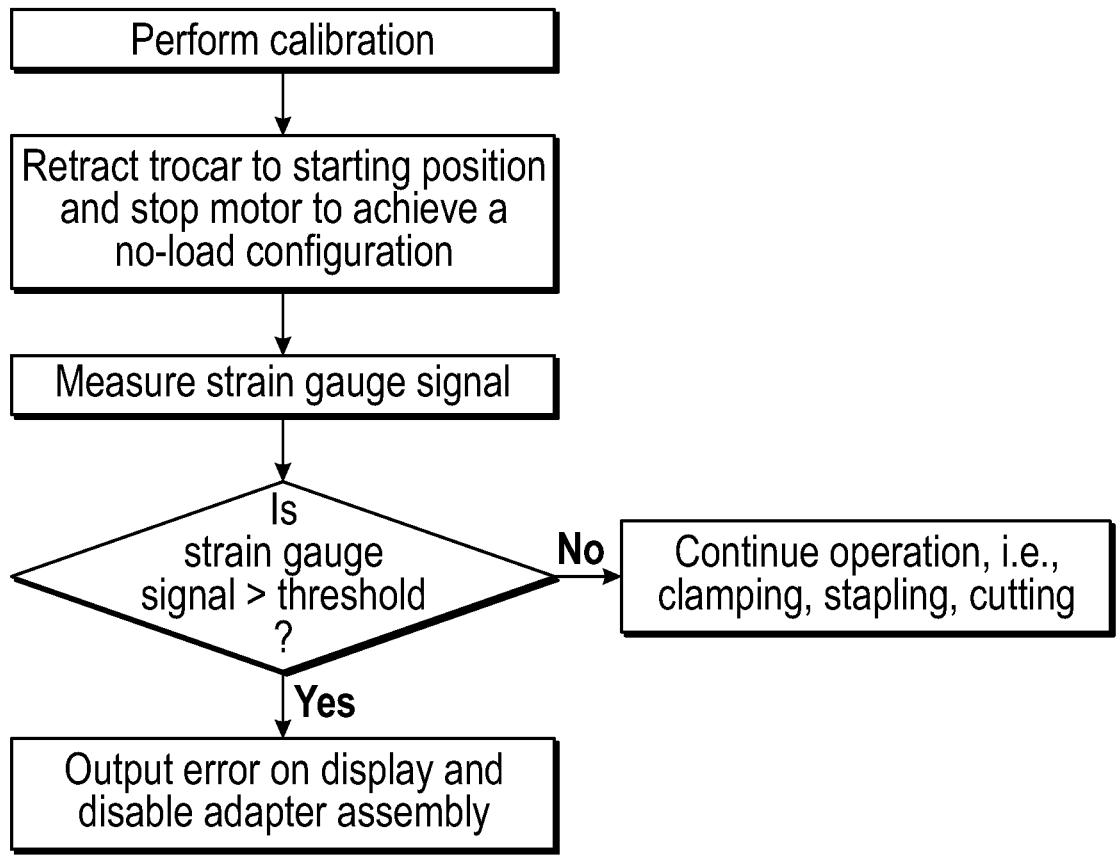
FIG. 8 is a method for monitoring a strain gauge of the surgical instrument of FIG. 1 according to an embodiment of the present disclosure.

With reference to FIG. 8, initially the powered surgical stapler 10 is calibrated. This may include calibrating the power handle 101 with the adapter assembly 200 alone and with the reload 400 attached to the adapter assembly 200. After calibration is performed, the trocar assembly 270, and in particular, the clamping transmission assembly 240, is retracted to a starting position prior to commencing the surgical procedure with the powered surgical stapler 10. At the starting position the trocar assembly 270 is stopped and is a "no-load" configuration, during which the trocar assembly 170 is under no mechanical load, e.g., not engaged with tissue which would normally impart strain or force on the trocar assembly 270. During the "no-load" configuration, the strain gauge 408*b* would be outputting a zero or a minimal sensor signal. In contrast, a malfunctioning strain gauge 408*b*, such as one that is subject to sensor drift due to environmental exposure or other factors, would output an erroneous sensor signal. Accordingly, the main controller 147 interrogates the strain gauge 408*b* while the trocar assembly 170 is disposed at the "no-load configuration." The main controller 147 compares the sensor signal to a threshold indicative of a fault in the strain gauge 408*b*. The main controller 147 may obtain an absolute value of the sensor signal and compare the absolute value of the sensor signal to the threshold.

If the sensor signal or the absolute thereof does not exceed the threshold, the powered surgical stapler 10 may be used to commence the surgical procedure, which may include introducing the powered surgical stapler 10 into the patient and perform the clamping, stapling, cutting processes. However, if sensor signal or the absolute thereof exceeds the threshold, which is indicative of the fault in the strain gauge 408*b*, then the main controller 147 outputs an error indicating the strain gauge 408*b* is faulty on the display 146. In addition, the main controller 147 prevents further operation of the powered surgical stapler 10 including operation of the motor 152 until a new adapter assembly 200 is attached to the power handle 101. The main controller 147 may write an error or fault code to the storage device 310, which would be read by the main controller 147 prior to use of the adapter assembly 200 preventing any subsequent use thereof.

It will be understood that various modifications may be made to the embodiments of the presently disclosed powered surgical staplers. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
    a motor;
    a transmission assembly movable by the motor;
    a force sensor configured to measure force imparted on the transmission assembly; and
    a controller configured to:
        control the motor to move the transmission assembly to a starting position;
        interrogate the force sensor to receive a sensor signal;
        compare the sensor signal to a threshold; and
        determine whether the force sensor is faulty based on the comparison of the sensor signal to the threshold.

2. The surgical device according to claim 1, wherein the force sensor is a strain gauge.

3. The surgical device according to claim 2, wherein the controller is further configured to determine whether the strain gauge has strain gauge drift.

4. The surgical device according to claim 2, wherein the starting position is a position at which the transmission assembly is under no mechanical load.

5. The surgical device according to claim 1, wherein the controller is further configured to obtain an absolute value of the sensor signal and compare the absolute value to the threshold.

6. The surgical device according to claim 1, further comprising a display.

7. The surgical device according to claim 6, wherein the controller is further configured to output an indication that the force sensor is faulty on the display.

8. The surgical device according to claim 1, wherein the controller is further configured to prevent operation of the motor in response to the force sensor being faulty.

9. The surgical device according to claim 1, further comprising:
a trocar assembly coupled to the transmission assembly.

10. The surgical device according to claim 1, further comprising:
a reload including a plurality of staples.

11. A surgical device comprising:
an adapter assembly including:
a transmission assembly; and
a force sensor configured to measure force imparted on the transmission assembly;
a handle assembly including:
a motor configured to move the transmission assembly; and
a controller configured to:
control the motor to move the transmission assembly to a starting position;
interrogate the force sensor to receive a sensor signal;
compare the sensor signal to a threshold; and
determine whether the force sensor is faulty based on the comparison of the sensor signal to the threshold.

12. The surgical device according to claim 11, wherein the force sensor is a strain gauge.

13. The surgical device according to claim 12, wherein the controller is further configured to determine whether the strain gauge has strain gauge drift.

14. The surgical device according to claim 12, wherein the starting position is a position at which the transmission assembly is under no mechanical load.

15. The surgical device according to claim 11, wherein the controller is further configured to obtain an absolute value of the sensor signal and compare the absolute value to the threshold.

16. The surgical device according to claim 11, further comprising a display and wherein the controller is further configured to output an indication that the force sensor is faulty on the display.

17. The surgical device according to claim 11, wherein the controller is further configured to prevent operation of the adapter assembly in response to the force sensor being faulty.

18. The surgical device according to claim 11, wherein the adapter assembly further includes a storage device and the controller is configured to store a fault code pertaining to force sensor being fault on the storage device.

19. The surgical device according to claim 11, further comprising:
a trocar assembly coupled to the transmission assembly.

20. The surgical device according to claim 11, further comprising:
a reload including a plurality of staples.

* * * * *